US009119969B2

(12) United States Patent
Vansickle

(10) Patent No.: US 9,119,969 B2
(45) Date of Patent: *Sep. 1, 2015

(54) SYSTEM AND METHOD FOR PROGRAMMING NEUROSTIMULATION DEVICES USING CACHED PLUG-IN SOFTWARE DRIVERS

(71) Applicant: BOSTON SCIENTIFIC NEUROMODULATION CORPORATION, Valencia, CA (US)

(72) Inventor: Dennis Allen Vansickle, Lancaster, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/321,667

(22) Filed: Jul. 1, 2014

(65) Prior Publication Data
US 2014/0316489 A1    Oct. 23, 2014

Related U.S. Application Data

(63) Continuation of application No. 13/474,237, filed on May 17, 2012, now Pat. No. 8,805,506.

(60) Provisional application No. 61/488,726, filed on May 21, 2011.

(51) Int. Cl.
*A61N 1/08* (2006.01)
*A61N 1/372* (2006.01)
*A61N 1/36* (2006.01)

(52) U.S. Cl.
CPC .......... *A61N 1/37235* (2013.01); *A61N 1/3605* (2013.01); *A61N 1/37247* (2013.01); *A61N 1/37264* (2013.01)

(58) Field of Classification Search
None
See application file for complete search history.

(56) References Cited

U.S. PATENT DOCUMENTS

| 5,168,871 | A | 12/1992 | Grevious |
| 6,236,917 | B1 | 5/2001 | Liebl et al. |
| 6,580,948 | B2 | 6/2003 | Haupert et al. |
| 6,839,650 | B2 | 1/2005 | Martin et al. |
| 6,895,280 | B2 | 5/2005 | Meadows et al. |
| 7,209,790 | B2 | 4/2007 | Thompson et al. |

(Continued)

OTHER PUBLICATIONS

U.S. Appl. No. 13/474,237, Non Final Office Action mailed Jul. 30, 2013, 7 pgs.

(Continued)

*Primary Examiner* — Brian T Gedeon
(74) *Attorney, Agent, or Firm* — Schwegman Lundberg & Woessner, P.A.

(57) ABSTRACT

A system for programming a plurality of different models, or generations, of neurostimulation devices includes a plurality of plug in software drivers stored on a hard drive of the system, wherein the plurality of plug-in software drivers are respectively configured for facilitating communication between the plurality of different models of neurostimulation devices and the system processor via a transceiver. In a method of programming a plurality of different models of neurostimulation devices, the system processor dynamically identifies the model of an interrogated neurostimulator and determines which plug-in software driver to use for programming the interrogated neurostimulator. The plug-in software drivers are cached into memory upon start-up of the system.

18 Claims, 5 Drawing Sheets

(56) References Cited

U.S. PATENT DOCUMENTS

| | | |
|---|---|---|
| 7,894,843 B2 | 2/2011 | Smart et al. |
| 8,805,506 B2 | 8/2014 | Vansickle |
| 2003/0028226 A1 | 2/2003 | Thompson et al. |
| 2007/0055324 A1 | 3/2007 | Thompson et al. |
| 2009/0216306 A1 | 8/2009 | Barker |
| 2010/0010566 A1 | 1/2010 | Thacker et al. |
| 2010/0083122 A1 | 4/2010 | Kozloski et al. |
| 2010/0121409 A1 | 5/2010 | Kothandaraman et al. |

OTHER PUBLICATIONS

U.S. Appl. No. 13/474,237, Non Final Office Action mailed Nov. 26, 2013, 13 pgs.

U.S. Appl. No. 13/474,237, Notice of Allowance mailed Apr. 1, 2014, 5 pgs.

U.S. Appl. No. 13/474,237, Response filed Feb. 4, 2014 to Non Final Office Action mailed Nov. 26, 2013, 11 pgs.

U.S. Appl. No. 13/474,237, Response filed Oct. 17, 2013 to Non Final Office Action mailed Jul. 30, 2013, 4 pgs.

SYSTEM AND METHOD FOR PROGRAMMING NEUROSTIMULATION DEVICES USING CACHED PLUG-IN SOFTWARE DRIVERS

RELATED APPLICATION DATA

The present application is a continuation of U.S. patent application Ser. No. 13/474,237, filed May 17, 2012, now issued as U.S. Pat. No. 8,805,506, which claims the benefit under 35 U.S.C. §119 to U.S. provisional patent application Ser. No. 61/488,726, filed on May 21, 2011, which applications are incorporated herein by reference.

FIELD OF THE INVENTION

The present invention relates to tissue stimulation systems, and more particularly, to a system and method for programming an implantable tissue stimulator.

BACKGROUND OF THE INVENTION

Implantable neurostimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications such as angina pectoralis and incontinence. Deep Brain Stimulation (DBS) has also been applied therapeutically for well over a decade for the treatment of refractory chronic pain syndromes, and DBS has also recently been applied in additional areas such as movement disorders and epilepsy. Further, in recent investigations Peripheral Nerve Stimulation (PNS) systems have demonstrated efficacy in the treatment of chronic pain syndromes and incontinence, and a number of additional applications are currently under investigation. Also, Functional Electrical Stimulation (FES) systems such as the Freehand system by NeuroControl (Cleveland, Ohio) have been applied to restore some functionality to paralyzed extremities in spinal cord injury patients.

These implantable neurostimulation systems typically include one or more electrode carrying neurostimulation leads, which are implanted at the desired stimulation site, and a neurostimulator (e.g., an implantable pulse generator (IPG)) implanted remotely from the stimulation site, but coupled either directly to the neurostimulation lead(s) or indirectly to the neurostimulation lead(s) via a lead extension. Thus, electrical pulses can be delivered from the neurostimulator to the neurostimulation leads to stimulate the tissue and provide the desired efficacious therapy to the patient. The neurostimulation system may further comprise a handheld patient programmer in the form of a remote control (RC) to remotely instruct the neurostimulator to generate electrical stimulation pulses in accordance with selected stimulation parameters. The RC may, itself, be programmed by a clinician, for example, by using a clinician's programmer (CP), which typically includes a general purpose computer, such as a laptop, with a programming software package installed thereon.

A clinician or physician may select between different models of neurostimulators to implant within the patient. Significant to the present inventions, each neurostimulation device model has its own programming software package. Thus, in order to be able to program a neurostimulation device, the clinician has to know which model the device is and has to know which programming software is associated with that particular device. If the clinician does not have the appropriate software installed on the CP, the clinician is unable to program that device model. Thus, when a new neurostimulation device model is developed, the developer must ensure that the associated programming software package is distributed to every clinician that may need to interact with the new model of the device. Further, a newly developed neurostimulation device, as well as its associated programming software package, is subjected to rigorous review and validation procedures by the FDA and other such regulatory agencies.

Thus, there remains a need for an easier, more convenient way to update programming software packages for neurostimulation systems.

SUMMARY OF THE INVENTION

In accordance with a first aspect of the present inventions, a system for programming a plurality of different models of neurostimulation devices includes: a memory; a hard drive; a transceiver configured for transmitting data to and from the plurality of different models of neurostimulation devices; a plurality of plug-in software drivers stored on the hard drive; and a processor configured for caching the plurality of plug-in software drivers in the memory, wherein the plurality of plug-in software drivers are respectively configured for facilitating communication between the plurality of different models of neurostimulation devices and the processor via the transceiver. The processor may be configured for interrogating a neurostimulator via the transceiver and determining which one of the plurality of plug-in software drivers corresponds to the interrogated neurostimulator. The system may further include a user interface configured for allowing a user to program the plurality of different models of neurostimulation devices.

In accordance with a second aspect of the present inventions, a system for programming a plurality of different models of neurostimulation devices includes: a hard drive; a transceiver configured for transmitting data to and from the plurality of different models of neurostimulation devices; a plurality of plug-in software drivers stored on the hard drive, wherein the plurality of plug-in software drivers are respectively configured for communicating with the plurality of different models of neurostimulation devices via the transceiver; and a processor configured for interrogating a neurostimulator via the transceiver and for determining which one of the plurality of plug-in software drivers corresponds to the interrogated neurostimulator, wherein the interrogated neurostimulator is one of the different models of neurostimulation devices with which the drivers are configured to communicate. The system may also include a memory, and the processor may be configured for caching the plurality of plug-in software drivers in the memory. Still further, the system may include a user interface configured for allowing a user to program the plurality of different models of neurostimulation devices.

In accordance with a third aspect of the present inventions, a method for programming a plurality of different models of neurostimulation devices using a system comprising a plurality of plug-in software drivers is provided. The method includes interrogating a neurostimulator. Interrogating the neurostimulator may include accessing a hard drive of the neurostimulator and obtaining identifying information from the hard drive of the interrogated neurostimulator. Before interrogating the neurostimulator, the method may include caching the plurality of plug-in software drivers into a memory of the system.

The method in accordance with the third aspect of the present inventions further includes: determining a model of the interrogated neurostimulator; based on the model of the neurostimulator, choosing one of the plug-in software drivers; and programming the interrogated neurostimulator using the chosen plug-in software driver. The method may further include using the chosen plug-in software driver to facilitate downloading information from the interrogated neurostimulator to the system.

Choosing one of the plug-in software drivers may include comparing the model of the interrogated neurostimulator to a model associated with each of the plug-in software drivers, wherein each of the plug-in software drivers is associated with a different model; determining that the model of the interrogated neurostimulator matches one of the models associated with one of the plug-in software drivers; and choosing the plug-in software driver associated with the matching model.

The method in accordance with the third aspect of the present inventions may further include: interrogating another neurostimulator; determining a model of the other interrogated neurostimulator; based on the model of the other interrogated neurostimulator, choosing another one of the plug-in software drivers; and programming the other interrogated neurostimulator via the other chosen plug-in software driver.

Still further, the method in accordance with the third aspect of the present inventions may include: interrogating another neurostimulator; determining a model of the other interrogated neurostimulator; comparing the model of the other interrogated neurostimulator to a model associated with each of the plurality of plug-in software drivers; determining that the model of other interrogated neurostimulator does not match any of the models associated with the plurality of plug-in software drivers; installing a new plug-in software driver on the system, wherein a model associated with the new plug-in software driver matches the model of the other interrogated neurostimulator; and programming the other interrogated neurostimulator via the new plug-in software driver.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

The description that follows relates to a spinal cord stimulation (SCS) system. However, it is to be understood that while the invention lends itself well to applications in SCS, the invention, in its broadest aspects, may not be so limited. Rather, the invention may be used with any type of implantable electrical circuitry used to stimulate tissue. For example, the present invention may be used as part of neurostimulation system, such as a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neural stimulator configured to treat urinary incontinence, sleep apnea, shoulder sublaxation, headache, etc.

Figure 1:
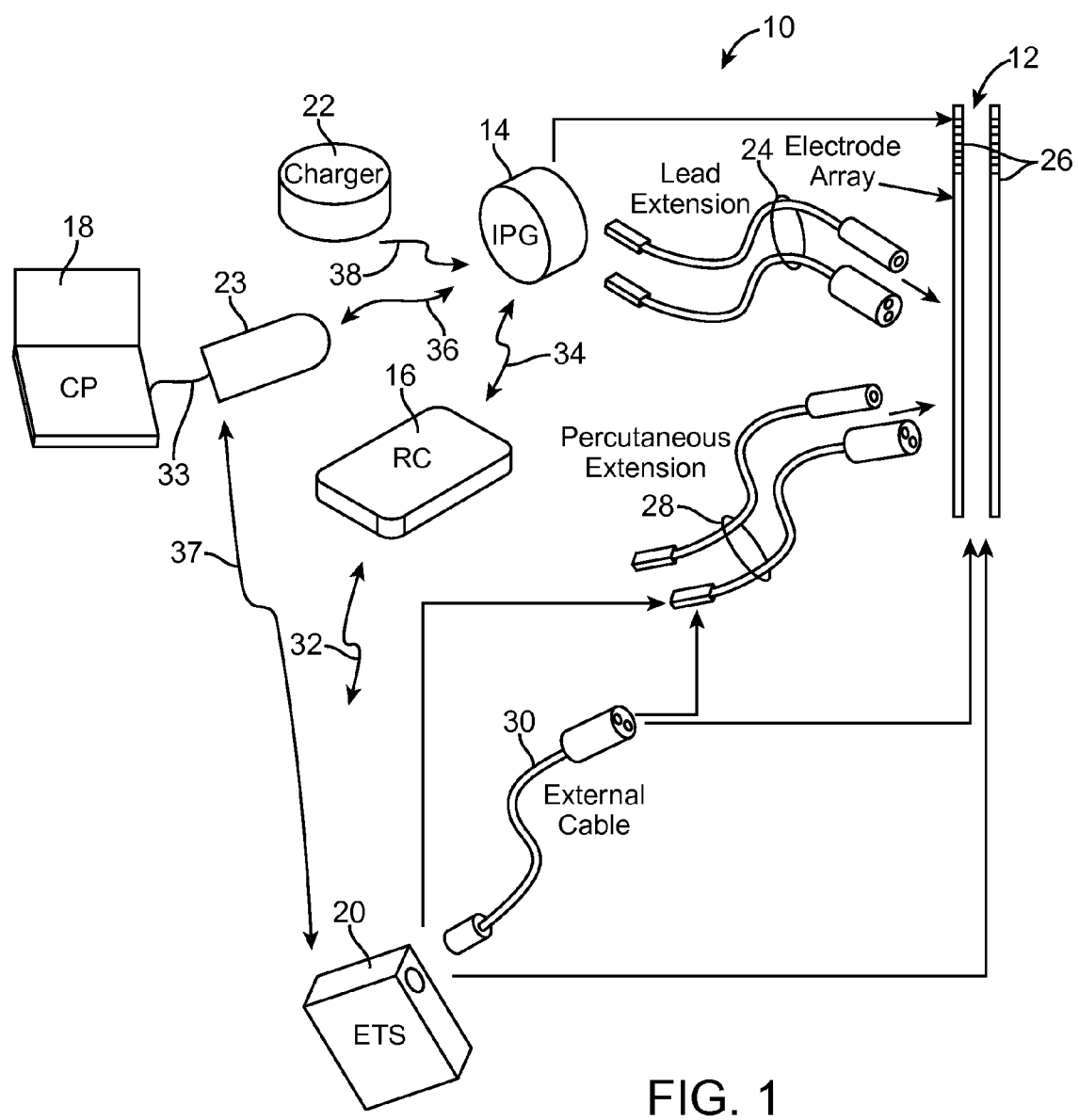
FIG. 1 is plan view of one embodiment of a spinal cord stimulation (SCS) system arranged in accordance with the present inventions.

Turning first to FIG. 1, an exemplary SCS system 10 generally comprises a plurality (in this case, two) of percutaneous neurostimulation leads 12, an implantable pulse generator (IPG) 14, an external remote control (RC) 16, a Clinician's Programmer (CP) 18, an External Trial Stimulator (ETS) 20, an external charger 22, and a transceiver 23.

The external charger 22 is a portable device used to transcutaneously charge the IPG 14 via an inductive link 38. For purposes of brevity, the details of the external charger 22 will not be described herein. Details of exemplary embodiments of external chargers are disclosed in U.S. Pat. No. 6,895,280, which is expressly incorporated herein by reference.

The IPG 14 is physically connected via two lead extensions 24 to the neurostimulation leads 12, which carry a plurality of electrodes 26 arranged in an array. The IPG 14 includes a replenishable power source, telemetry circuitry, and pulse generation circuitry that delivers electrical stimulation energy in the form of a pulsed electrical waveform (i.e., a temporal series of electrical pulses) to the electrode array 26 in accordance with a set of stimulation parameters. The IPG 14 and neurostimulation leads 12 can be provided as an implantable neurostimulation kit, along with, e.g., a hollow needle, a stylet, a tunneling tool, and a tunneling straw. Further details discussing implantable kits are disclosed in U.S. Patent Publication 2009/0216306, entitled "Temporary Neurostimulation Lead Identification Device," which is expressly incorporated herein by reference.

The ETS 20 may also be physically connected via percutaneous lead extensions 28 and external cable 30 to the neurostimulation leads 12. The ETS 20, which has pulse generation circuitry similar to that of the IPG 14, also delivers electrical stimulation energy in the form of a pulsed electrical waveform to the electrode array 26 in accordance with a set of stimulation parameters. The major difference between the ETS 20 and the IPG 14 is that the ETS 20 is a non-implantable device that is used on a trial basis after the neurostimulation leads 12 have been implanted and prior to implantation of the IPG 14, to test the responsiveness of the stimulation that is to be provided. Further details of an exemplary ETS are described in U.S. Pat. No. 6,895,280, which has been previously incorporated herein by reference.

The RC 16 may be used to telemetrically control the ETS 20 via a bi-directional RF communications link 32. Once the IPG 14 and neurostimulation leads 12 are implanted, the RC 16 may be used to telemetrically control the IPG 14 via a bi-directional RF communications link 34. Such control allows the IPG 14 to be turned on or off and to be programmed with different stimulation programs after implantation. Once the IPG 14 has been programmed, and its power source has been charged by the external charger 22 or otherwise replenished, the IPG 14 may function as programmed without the RC 16 being present.

The CP 18 provides clinician detailed stimulation parameters for programming the IPG 14 and ETS 20 in the operating room and in follow-up sessions. The CP 18 may perform this function by indirectly communicating with the IPG 14 or ETS 20, through the transceiver 23. In particular, the CP 18 communicates with the transceiver 23 via a cable 33, and the transceiver 23 communicates with the IPG 14 via a bi-directional RF link 36, and with the ETS 20 via a bi-directional RF link 37.

In the illustrated embodiment, the transceiver 23 is embodied as an external wand that connects to the CP 18 through a cable 33. The cable 33 takes the form of a USB cable that includes connectors (not shown) on opposite ends to respectively connect to a USB port on the transceiver 23 and a corresponding USB port (not shown) on the CP 18. Alternatively, the transceiver 23 may connect to the CP 18 through a bi-directional wireless (e.g., IR, RF, etc.) connection, or may be integrated into the CP 18. The transceiver 23 is capable of being placed in proximity to the IPG 14 (e.g., within four feet), thereby allowing the CP 18 to program and receive status information from the IPG 14.

Figure 2:
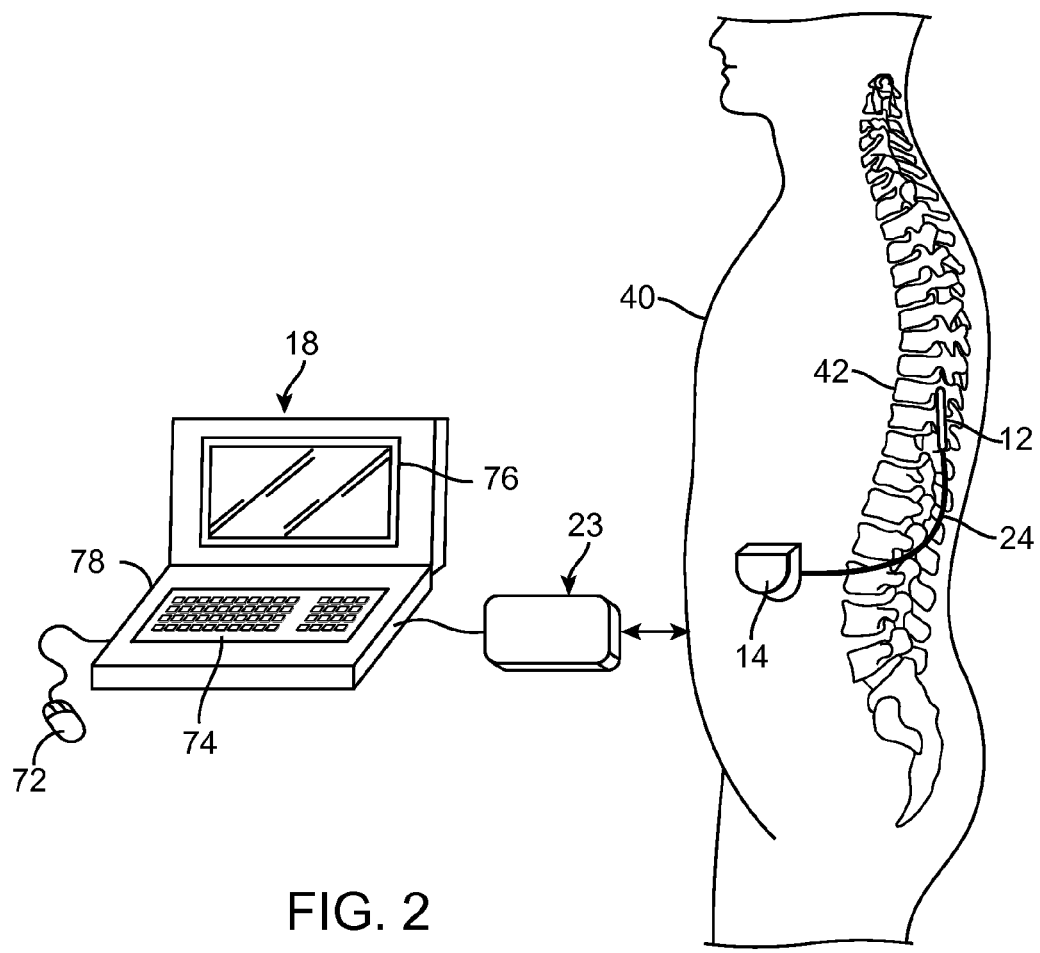
FIG. 2 is a plan view of the SCS system of FIG. 1 in use with a patient.

Referring to FIG. 2, the neurostimulation leads 12 are implanted within the spinal column 46 of a patient 48. The preferred placement of the neurostimulation leads 12 is adjacent, i.e., resting near, or upon the dura, adjacent to the spinal cord area to be stimulated. Due to the lack of space near the location where the neurostimulation leads 12 exit the spinal column 46, the IPG 14 is generally implanted in a surgically-made pocket either in the abdomen or above the buttocks. The IPG 14 may, of course, also be implanted in other locations of the patient's body. The lead extensions 24 facilitate locating the IPG 14 away from the exit point of the neurostimulation leads 12. As there shown, the CP 18 communicates with the IPG 14 via the transceiver 23. While the neurostimulation leads 12 are illustrated as being implanted near the spinal cord area of a patient, the neurostimulation leads 12 may be implanted anywhere in the patient's body, including a peripheral region, such as a limb, or the brain. After implantation, the IPG 14 is used to provide the therapeutic stimulation under control of the patient.

Figure 3:
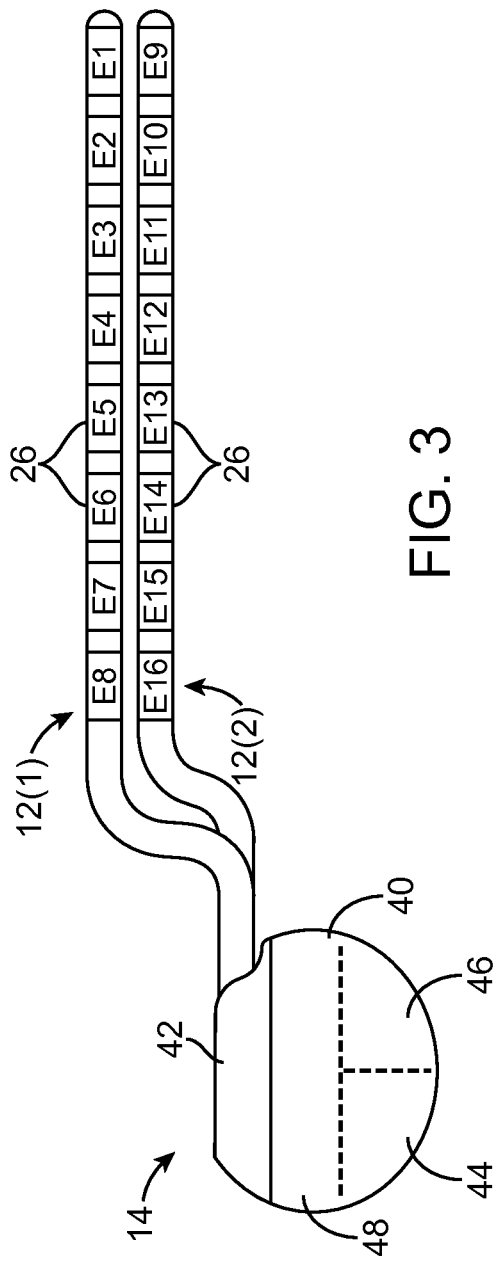
FIG. 3 is a side view of an implantable pulse generator and a pair of stimulation leads that can be used in the SCS system of FIG. 1.

Referring now to FIG. 3, some of the features of the neurostimulation leads 12 and the IPG 14 will be briefly described. One of the neurostimulation leads 12(1) has eight electrodes 26 (labeled E1-E8), and the other stimulation lead 12(2) has eight electrodes 26 (labeled E9-E16). The actual number and shape of leads and electrodes will, of course, vary according to the intended application. The IPG 14 comprises an outer case 40 for housing the electronic and other components (some of which are shown in phantom and described in further detail below), and a connector 42 to which the proximal ends of the neurostimulation leads 12 mate in a manner that electrically couples the electrodes 26 to the electronics within the outer case 40. The outer case 40 is composed of an electrically conductive, biocompatible material, such as titanium, and forms a hermetically sealed compartment for protecting the internal electronics from the body tissue and fluids. In some cases, the outer case 40 may serve as an electrode.

The IPG 14 includes a battery 44 and pulse generation circuitry 46 that delivers the electrical stimulation energy in the form of a pulsed electrical waveform to the electrode array 26 in accordance with a set of stimulation parameters programmed into the IPG 14. Such stimulation parameters may comprise electrode combinations, which define the electrodes that are activated as anodes (positive), cathodes (negative), and turned off (zero), percentage of stimulation energy assigned to each electrode (fractionalized electrode configurations), and electrical pulse parameters, which define the pulse amplitude (measured in milliamps or volts depending on whether the IPG 14 supplies constant current or constant voltage to the electrode array 26), pulse width (measured in microseconds), and pulse rate (measured in pulses per second).

Electrical stimulation will occur between two (or more) activated electrodes, one of which may be the IPG case 40. Simulation energy may be transmitted to the tissue in a monopolar or multipolar (e.g., bipolar, tripolar, etc.) fashion. Monopolar stimulation occurs when a selected one of the lead electrodes 26 is activated along with the case 40 of the IPG 14, so that stimulation energy is transmitted between the selected electrode 26 and the case 40. Bipolar stimulation occurs when two of the lead electrodes 26 are activated as anode and cathode, so that stimulation energy is transmitted between the selected electrodes 26. For example, electrode E3 on the first lead 12 may be activated as an anode at the same time that electrode E11 on the second lead 12 is activated as a cathode. Tripolar stimulation occurs when three of the lead electrodes 26 are activated, two as anodes and the remaining one as a cathode, or two as cathodes and the remaining one as an anode. For example, electrodes E4 and E5 on the first lead 12 may be activated as anodes at the same time that electrode E12 on the second lead 12 is activated as a cathode.

The IPG 14 also includes a hard drive 48 that stores programming data and identifying information. Examples of such identifying information stored on the hard drive 48 may include patient name, patient date of birth, hardware model, hardware serial number, firmware information, etc. When the IPG 14 is interrogated by the CP 18 via the transceiver 23, hardware recognition occurs. That is, the hard drive 48 is accessed and the identifying information stored in the hard drive 48 is transmitted to the CP 18 via the transceiver 23.

As briefly discussed above, the CP 18 greatly simplifies the programming of multiple electrode combinations, allowing the user (e.g., the physician or clinician) to readily determine the desired stimulation parameters to be programmed into the IPG 14, as well as the RC 16. Thus, modification of the stimulation parameters in the programmable memory of the IPG 14 after implantation is performed by a user using the CP 18, which can indirectly communicate with the IPG 14 via the transceiver 23. That is, the CP 18 can be used by the user to modify operating parameters of the electrode array 26.

Referring back to FIG. 2, the overall appearance of the CP 18 is that of a laptop personal computer (PC), and in fact, may be implemented using a PC that has been appropriately configured to include a directional-programming device and programmed to perform the functions described herein. Thus, the programming methodologies can be performed by executing software instructions contained within the CP 18. Alternatively, such programming methodologies can be performed using firmware or hardware. In any event, the CP 18 may actively control the characteristics of the electrical stimulation generated by the IPG 14 (or ETS 20) to allow the optimum stimulation parameters to be determined based on patient feedback and for subsequently programming the IPG 14 (or ETS 20) with the optimum stimulation parameters.

To allow the user to perform these functions, the CP 18 includes a mouse 72, a keyboard 74, and a display screen 76 housed in a case 78. In the illustrated embodiment, the display screen 76 is a conventional screen. It is to be understood that in addition to, or in lieu of, the mouse 72, other directional programming devices may be used, such as a trackball, touchpad, or joystick. Alternatively, the display screen 76 may be a digitizer screen, such as a touch screen (not shown), which may be used in conjunction with an active or passive digitizer stylus/finger touch.

A conventional CP is able to communicate with only one type, or model, of neurostimulation device. That is, because each model of neurostimulation device requires its own programming software package, switching from one model of neurostimulation device to another model required switching programming software packages.

A CP 18 in accordance with the present inventions is configured for programming a plurality of different models of neurostimulation devices as described in more detail below. Thus, regardless of which model of neurostimulation device a patient has, the CP 18 is capable of programming the patient's neurostimulation device. The "model" of neurostimulation device refers to the version, or generation, of the device. For example, a neurostimulation device may be a first generation device, a second generation device, a third generation device, etc. One of the advantages of the present invention is that the CP 18 is easily adapted to support future generations of neurostimulation devices.

Figure 4:
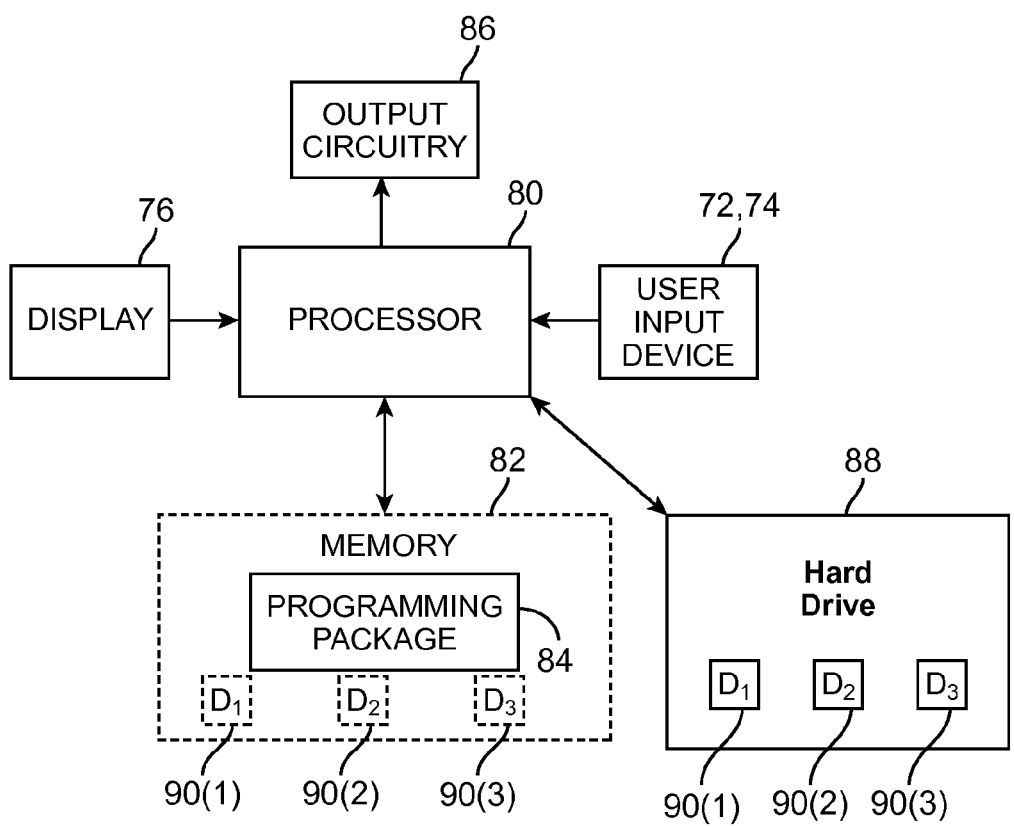
FIG. 4 is a block diagram of the components of the clinician programmer that can be used in the SCS system of FIG. 1.

As shown in FIG. 4, the CP 18 in accordance with the present inventions generally includes a processor 80 (e.g., a central processor unit (CPU)) and memory 82 that stores a stimulation programming package 84, which can be executed by the processor 80 to allow the user to program the IPG 14 or the ETS 20. The CP 18 further includes output circuitry 86 for downloading stimulation parameters to the IPG 14 or the ETS 20.

The CP 18 also includes a hard drive 88 and plug-in software drivers 90. In the illustrated embodiment, the plug-in software drivers 90 are dynamic link library (DLL) plug-ins that act as "translators" between the neurostimulation devices (i.e., IPGs 14 or ETSs 20) and the programming package 84. Each different model, or generation, of neurostimulation device has its own specialized set of commands. The device driver DLL 90 for each model of neurostimulation device is configured to translate generic commands issued by the programming package 84 into the specialized commands understood by that model of neurostimulation device. The DLL plug-ins 90 are also configured to retrieve information from the neurostimulators, and transmit the information, properly translated, to the programming package 84.

Thus, the DLL plug-in drivers 90 facilitate communication between the processor 80 operating in accordance with the programming package 84 and the different models of neurostimulation devices. By isolating this "translation" function in the DLL plug-ins 90, new generations of neurostimulation devices are able to use the same programming package 84 as older generations of neurostimulation devices, so long as a DLL plug-in 90 corresponding to the new generation device is installed on the CP 18. Thus, each new model of neurostimulation device does not require an entirely new programming software package. Rather, the new model of neurostimulation device just requires a new plug-in driver to be installed on the CP 18, which is already being used to program older versions of neurostimulation devices. Updates made to the driver do not affect the rest of the programming software package 84. In this manner, the review and validation by the FDA and other such regulatory agencies of the new model of neurostimulation device and its associated software are streamlined.

Although three drivers 90(1), 90(2), and 90(3) are depicted, it should be well understood that the CP 18 may include more or less drivers 90. In particular, the number of drivers 90 corresponds to the number of neurostimulation device models that the CP 18 is configured to program. For example, if four generations of neurostimulation device models have been developed, the CP 18 would include four drivers 90 in order to be able to program each model of neurostimulation device. Each of the drivers 90 corresponds to one of the neurostimulation device models. As discussed in more detail below, based on an initial interrogation of a neurostimulation device, the processor 80 dynamically determines which model the interrogated neurostimulator is, and then chooses the software plug-in driver 90 corresponding to that model.

As shown in FIG. 4, the drivers 90 are stored on the hard drive 88 of the CP 18. However, because the drivers 90 are frequently accessed, upon start-up of the CP 18, the drivers 90 are cached into memory 82, as shown in phantom in FIG. 4. Automatically caching the drivers 90 into memory 82 upon start up of the CP 18 improves processing speed because the drivers are quickly and easily accessed in the cache memory.

Execution of the programming package 84 by the processor 80 provides a multitude of display screens (not shown) that can be navigated through via use of the mouse 72. These display screens allow the clinician to, among other functions, select or enter patient profile information (e.g., name, birth date, patient identification, physician, diagnosis, and address), enter procedure information (e.g., programming/follow-up, implant trial system, implant IPG, implant IPG and lead(s), replace IPG, replace IPG and leads, replace or revise leads, explant, etc.), generate a pain map of the patient, define the configuration and orientation of the leads, initiate and control the electrical stimulation energy output by the leads 12, and select and program the IPG 14 with stimulation parameters in both a surgical setting and a clinical setting. One of the advantages of the present invention is that these display screens, or user interfaces, are the same regardless of the model of the neurostimulation device being programmed. As such, clinicians comfortable with the user interface of the CP 18 will be able to program next generation and future generation neurostimulators because the user interface will remain the same. Further details discussing the above-described CP functions are disclosed in U.S. patent application Ser. No. 12/501,282, entitled "System and Method for Converting Tissue Stimulation Programs in a Format Usable by an Electrical Current Steering Navigator," and U.S. patent application Ser. No. 12/614,942, entitled "System and Method for Determining Appropriate Steering Tables for Distributing Stimulation Energy Among Multiple Neurostimulation Electrodes," which are expressly incorporated herein by reference.

Figure 5:
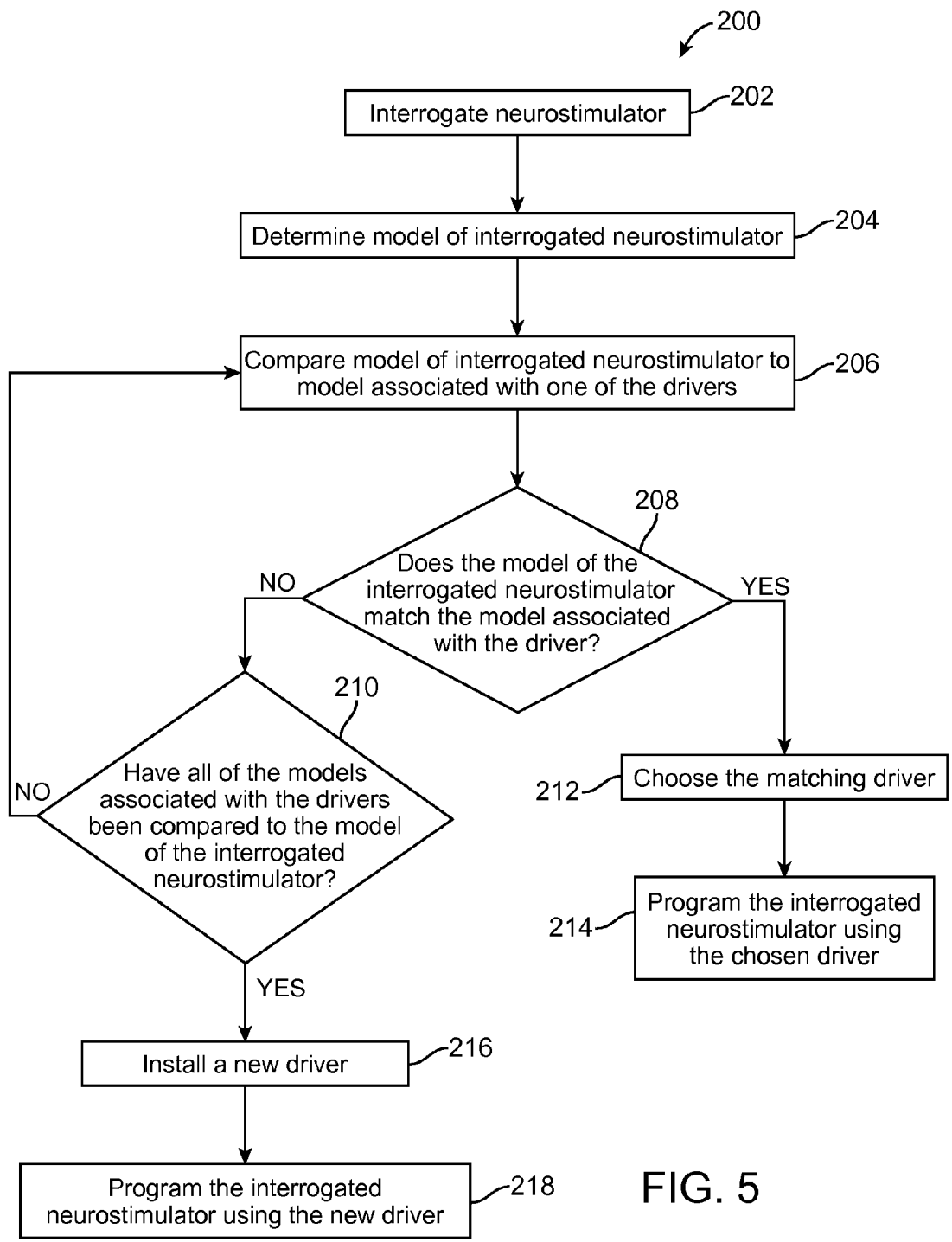
FIG. 5 is a flow chart of a method for programming a plurality of different models of neurostimulation devices.

FIG. 5 depicts a method 200 for programming a plurality of different models of neurostimulation devices using the system 10 shown in FIG. 1. First, in step 202, a neurostimulator is interrogated by the CP 18 via the transceiver 23. The interrogated neurostimulator may be an IPG 14 or an ETS 20. When the IPG 14 or the ETS 20 is in contact with the CP 18, hardware information is uploaded to the CP 18 via the transceiver 23. That is, during the interrogation, the hard drive of the neurostimulator is accessed and identifying information about the neurostimulator is obtained from the hard drive and transmitted to the CP 18.

Based on the identifying information, in step 204, the processor 80 of the CP 18 determines the model of the interrogated neurostimulator. Next, in step 206, the processor 80 compares the model of the interrogated stimulator to the model associated with one of the drivers 90. Each one of the drivers 90 is associated with a different model of neurostimulation device. For example, driver 90(1) may be associated with first generation neurostimulation devices, driver 90(2) may be associated with second generation neurostimulation devices, driver 90(3) may be associated with third generation neurostimulation devices, and so on. If the model associated with the driver matches the model of the interrogated stimulator (i.e., if the answer to decision block 208 is "yes"), then that driver is chosen in step 212. For example, if the identifying information obtained from the interrogated neurostimulator indicates that the interrogated neurostimulator is a second generation device, driver 90(2) would be chosen in step 212. The chosen driver 90 is then used during programming of the interrogated stimulator in step 214.

However, if it is determined in step 208 that the model associated with the driver does not match the model of the interrogated neurostimulator, then the comparison is performed with the next driver. The comparison step 206 is repeated with each driver 90 until a match is found between the model of the interrogated neurostimulator and the model associated with the driver.

If, in step 210, it is determined that all of the drivers 90 have been compared to the model of the interrogated neurostimulator (i.e., if the answer to decision block 210 is "yes"), and no match was found, then a new driver is installed in step 216. The model associated with the new driver matches the model of the interrogated neurostimulator. The new driver may be deployed to the CP 18 via any deployment methodology, such as by downloading, installing from a CD, installing from a thumb drive, or the like. Finally, in step 218, the interrogated neurostimulator is programmed using the newly installed driver.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A method for communicating with one of a plurality of neurostimulation devices respectively of different models, the method comprising:
   caching a plurality of plug-in software drivers from a hard drive into memory, the plurality of plug-in software drivers respectively corresponding to the different models;
   selecting one of the plug-in software drivers from the memory; and
   communicating with the one neurostimulation device using the selected plug-in software driver.

2. The method of claim 1, further comprising interrogating the one neurostimulation device, wherein the one plug-in software driver corresponding to the model of the interrogated neurostimulation device model is selected.

3. The method of claim 1, further comprising programming the one neurostimulation device using the selected plug-in software driver.

4. The method of claim 3, wherein the plug-in software drivers are dynamic link library (DLL) plug-ins, and the programming of the one neurostimulation device comprises issuing generic commands, and using the chosen DLL plug-in to translate the generic commands into specialized commands to program the neurostimulation device.

5. A method for communicating with one of a plurality of neurostimulation devices respectively of different models, the method comprising:
   interrogating the one neurostimulation device;
   determining the model of the interrogated neurostimulation device;
   selecting one of a plurality of plug-in software drivers respectively corresponding to the plurality of different models, wherein the one plug-in software driver is selected based on the determined one neurostimulation device; and
   communicating with the one neurostimulation device using the selected plug-in software driver.

6. The method of claim 5, further comprising programming the one neurostimulation device using the selected plug-in software driver.

7. The method of claim 5, further comprising downloading information from the one neurostimulation device using the selected plug-in software driver.

8. The method of claim 5, wherein interrogating the one neurostimulation device comprises accessing a hard drive of the one neurostimulation device and obtaining identifying information from the hard drive of the one interrogated neurostimulator.

9. The method of claim 5, wherein selecting the one plug-in software drivers comprises:
   comparing the model of the interrogated neurostimulator to the model associated with the plug-in software drivers;
   determining that the model of the interrogated neurostimulator matches one of the models associated with one of the plug-in software drivers; and
   selecting the plug-in software driver associated with the matching model.

10. The method of claim 5,
   interrogating another one of the neurostimulation devices;
   determining the model of the other interrogated neurostimulation device;
   selecting another one of a plurality of plug-in software drivers based on the determined one other neurostimulation device; and
   communicating with the one other neurostimulation device using the other selected plug-in software driver.

11. The method of claim 5, further comprising, before interrogating the one neurostimulation device, caching the plurality of plug-in software drivers from a hard drive into memory.

12. The method of claim 5, wherein the plug-in software drivers are dynamic link library (DLL) plug-ins, and the programming of the one neurostimulation device model comprises issuing generic commands, and using the chosen DLL plug-in to translate the generic commands into specialized commands to program the neurostimulation device model.

13. A method for communicating with one of a plurality of neurostimulation devices respectively of different models, the method comprising:

interrogating the one neurostimulation device;
determining the model of the interrogated neurostimulation device;
selecting one of a plurality of plug-in software drivers respectively corresponding to the plurality of different models, wherein the one plug-in software driver is selected based on the determined one neurostimulation device;
communicating with the one neurostimulation device using the selected plug-in software driver;
programming the one neurostimulation device using the selected plug-in software driver; and
downloading information from the one neurostimulation device using the selected plug-in software driver.

14. The method of claim 13, wherein interrogating the one neurostimulation device comprises accessing a hard drive of the one neurostimulation device and obtaining identifying information from the hard drive of the one interrogated neurostimulator.

15. The method of claim 13, wherein selecting the one plug-in software drivers comprises:
   comparing the model of the interrogated neurostimulator to the model associated with the plug-in software drivers;
   determining that the model of the interrogated neurostimulator matches one of the models associated with one of the plug-in software drivers; and
   selecting the plug-in software driver associated with the matching model.

16. The method of claim 13,
interrogating another one of the neurostimulation devices;
determining the model of the other interrogated neurostimulation device;
selecting another one of a plurality of plug-in software drivers based on the determined one other neurostimulation device; and
communicating with the one other neurostimulation device using the other selected plug-in software driver.

17. The method of claim 13, further comprising, before interrogating the one neurostimulation device, caching the plurality of plug-in software drivers from a hard drive into memory.

18. The method of claim 13, wherein the plug-in software drivers are dynamic link library (DLL) plug-ins, and the programming of the one neurostimulation device model comprises issuing generic commands, and using the chosen DLL plug-in to translate the generic commands into specialized commands to program the neurostimulation device model.

* * * * *